(12) United States Patent
Suter

(10) Patent No.: US 6,516,677 B1
(45) Date of Patent: Feb. 11, 2003

(54) SAMPLING VALVE AND DEVICE FOR LOW-LOSS SAMPLING OF FLUID FROM THE INTERIOR OF A HOLLOW BODY, PARTICULARLY OF A CONTAINER OR LINE

(75) Inventor: Nicolai Suter, Zürich (CH)

(73) Assignee: Nisco Engineering AG, Zurich (CH)

( * ) Notice: Subject to any disclaimer, the term of this patent is extended or adjusted under 35 U.S.C. 154(b) by 0 days.

(21) Appl. No.: 09/550,023

(22) Filed: Apr. 14, 2000

(30) Foreign Application Priority Data

Apr. 14, 1999 (CH) ................................................ 0689/99

(51) Int. Cl.[7] ................................................ G01N 1/00
(52) U.S. Cl. ................................................ 73/863.85
(58) Field of Search .................. 73/863.44, 863.54, 73/863.55, 863.57, 863.71, 863.82, 863.86, 863.85; 251/319, 333

(56) References Cited

U.S. PATENT DOCUMENTS 4,669,321 A * 6/1987 Meyer ...................... 73/863.85
5,296,197 A * 3/1994 Newbert et al. .......... 73/863.86

FOREIGN PATENT DOCUMENTS

| EP | 350723 | 6/1989 |
| FR | 0 752 936 | 3/1998 |
| GB | 2 220 250 | 1/1990 |

* cited by examiner

Primary Examiner—Robert Raevis
(74) Attorney, Agent, or Firm—Browdy and Neimark

(57) ABSTRACT

A sampling valve (1), which is mounted on a container (5) has a valve stem (15) with a longitudinal bore (25), the front end of which opens into a cross bore (26) and is guided on this end in a sealed-tight manner inside an opening (7). The stem (15) is slidable between two positions by means of a lifting device (21). In the one end position the cross bore (26) opens into the interior space (6) of the container (5), in the other it opens into a valve chamber (10). The other end of the longitudinal bore (25) communicates with a nozzle (27), which is connected to an autosampler (72) via lines (67, 68) and a valve (70). The chamber (10) is connected to three valves (51–53) via a nozzle (33). The chamber (10) can be supplied with steam for sterilization purposes via the valve (51), and with sterile gas for transporting the extracted sample to the autosampler (72) via the valve (53). The device permits a practically loss-free, automatic, periodic extraction of small fluid samples from the container (5).

24 Claims, 4 Drawing Sheets

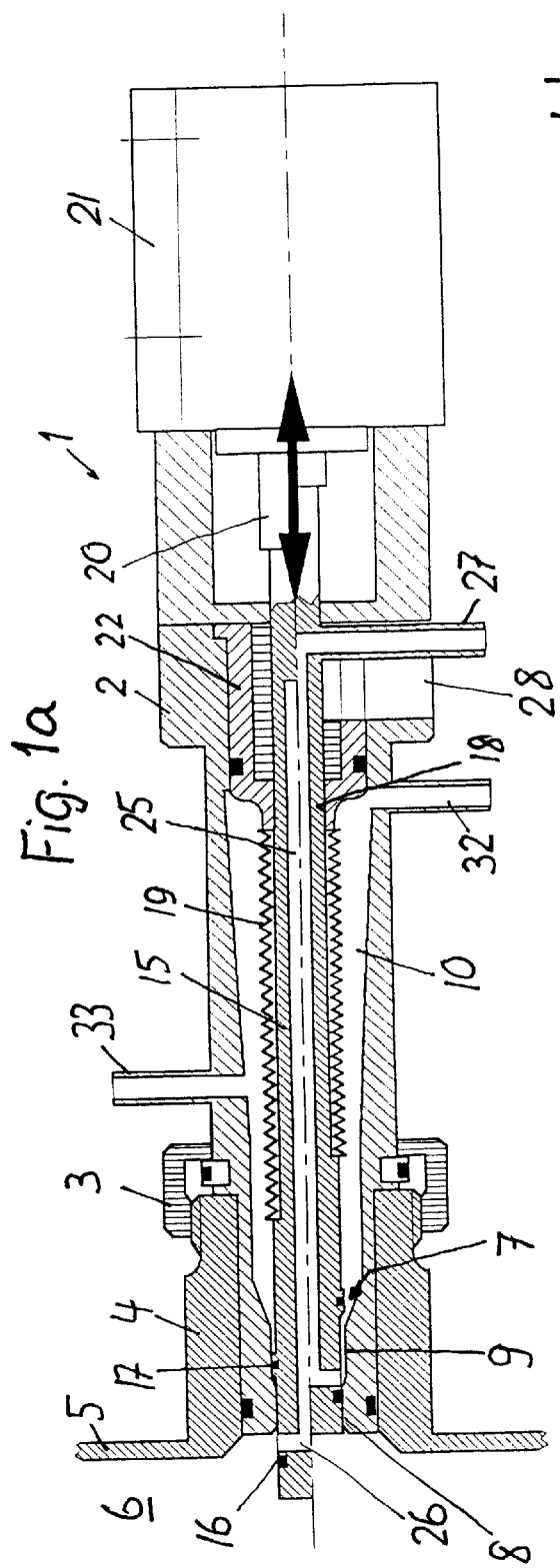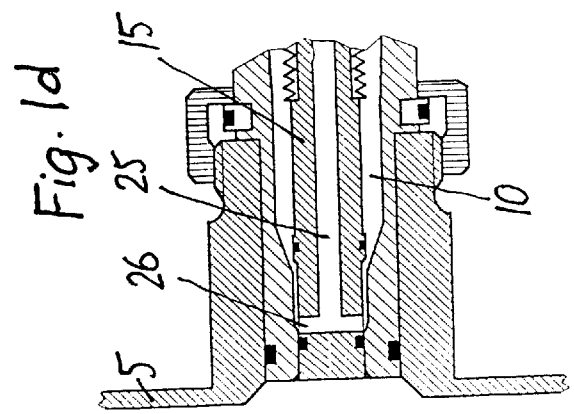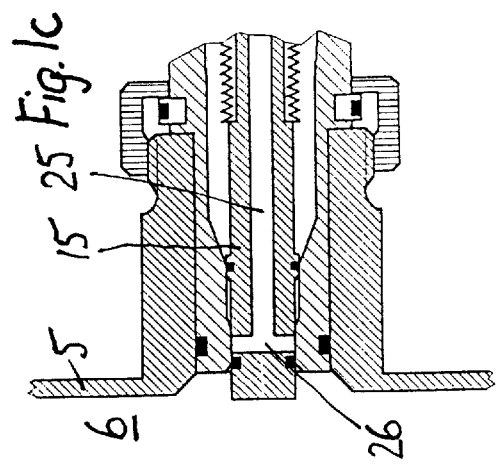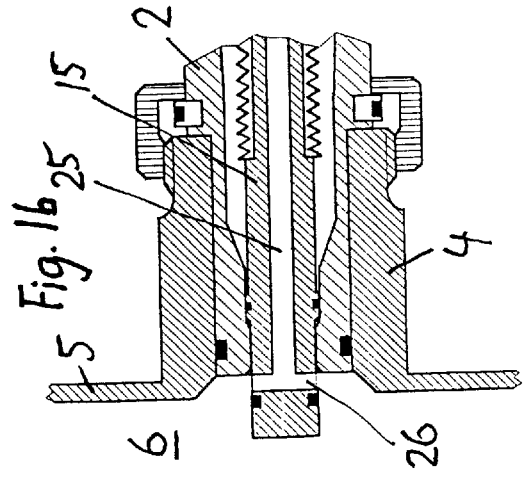

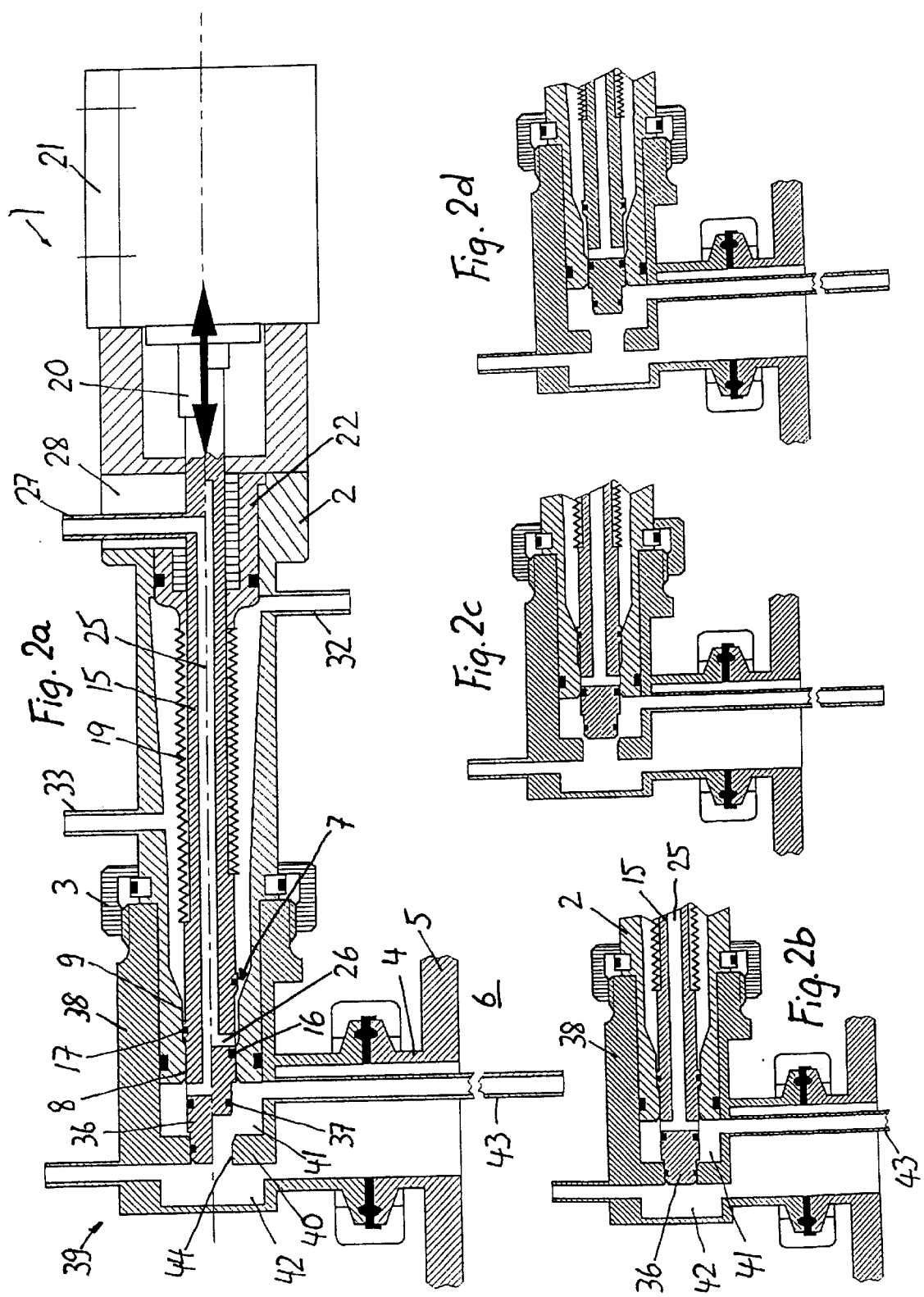

SAMPLING VALVE AND DEVICE FOR LOW-LOSS SAMPLING OF FLUID FROM THE INTERIOR OF A HOLLOW BODY, PARTICULARLY OF A CONTAINER OR LINE

FIELD OF THE INVENTION

The present invention relates to low-loss sampling and especially a device for low-loss sampling.

BACKGROUND

A sampling valve is known from EP-A-350 723 with a casing mounted on a container or line. The casing has an axial bore inside of which a valve stem is movably maintained. In one embodiment, the valve stem has a longitudinal bore, which, adjacent to its unattached end, opens into a continuous cross bore. Placed on both sides of the cross bore are sealing rings in grooves on the valve stem. The stem is positionable into a first position in which the cross bore projects into the interior space of the container and into a second position, in which it is sealed. In the first position a sample can be extracted through the longitudinal bore.

This prior sampling valve can be cleaned and sterilized only together with the container or after dismantling. Automatic, periodic sampling during an ongoing process is not possible with this sampling valve.

Sampling is very common in sterile process technology (pharmaceutical engineering and bio-engineering).

Growing demands in production (process control, archiving of samples), as well as in process development, are promoting the development of new, improved systems. The products are becoming increasingly more expensive and the production volumes tend to become smaller. Furthermore, Modern analysis methods make it possible to use increasingly smaller samples. This has created a demand for increasingly smaller extracted quantities and a requirement to keep losses, including losses due to sampling, at a minimum, especially in the field of process development where there is a demand for regular sampling in the 24-hour operation. Another application in sterile production is the sampling from product-transporting lines.

SUMMARY OF THE INVENTION

The present invention is based on the objective of taking, under sterile conditions, a sample of a defined volume from a sterile tank or a sterile line of fluid. The objective is to take the sample, e.g. a defined volume from the fluid, either via a nozzle or an immersion pipe. This defined volume is to be ejected as completely as possible during a second step and transported to a removal location. This removal location could be a sterile packing drum or automatic sterile filling machine, which, for example, stores the samples refrigerated (autosampler), or it could be an automatic analysis machine (e.g., with sample processing, with gas chromatographs and with automatic processing of the measured values). In a third step, the system must be cleaned in place (CIP) and sterilized in place (SIP). The objective is to make this cycle reproducible and repeatable as often as desired without jeopardizing the sterile operation.

BRIEF DESCRIPTION OF DRAWINGS

Exemplary embodiments of the invention are explained below based on the drawings, in which:

FIG. 1a shows a first example embodiment of a sampling valve,

FIGS. 1b through 1d show sections from the illustration in FIG. 1a in three different positions, FIGS. 2a through 2d show corresponding illustrations of a second embodiment.

DETAILED DESCRIPTION OF EMBODIMENTS

Figure 3:
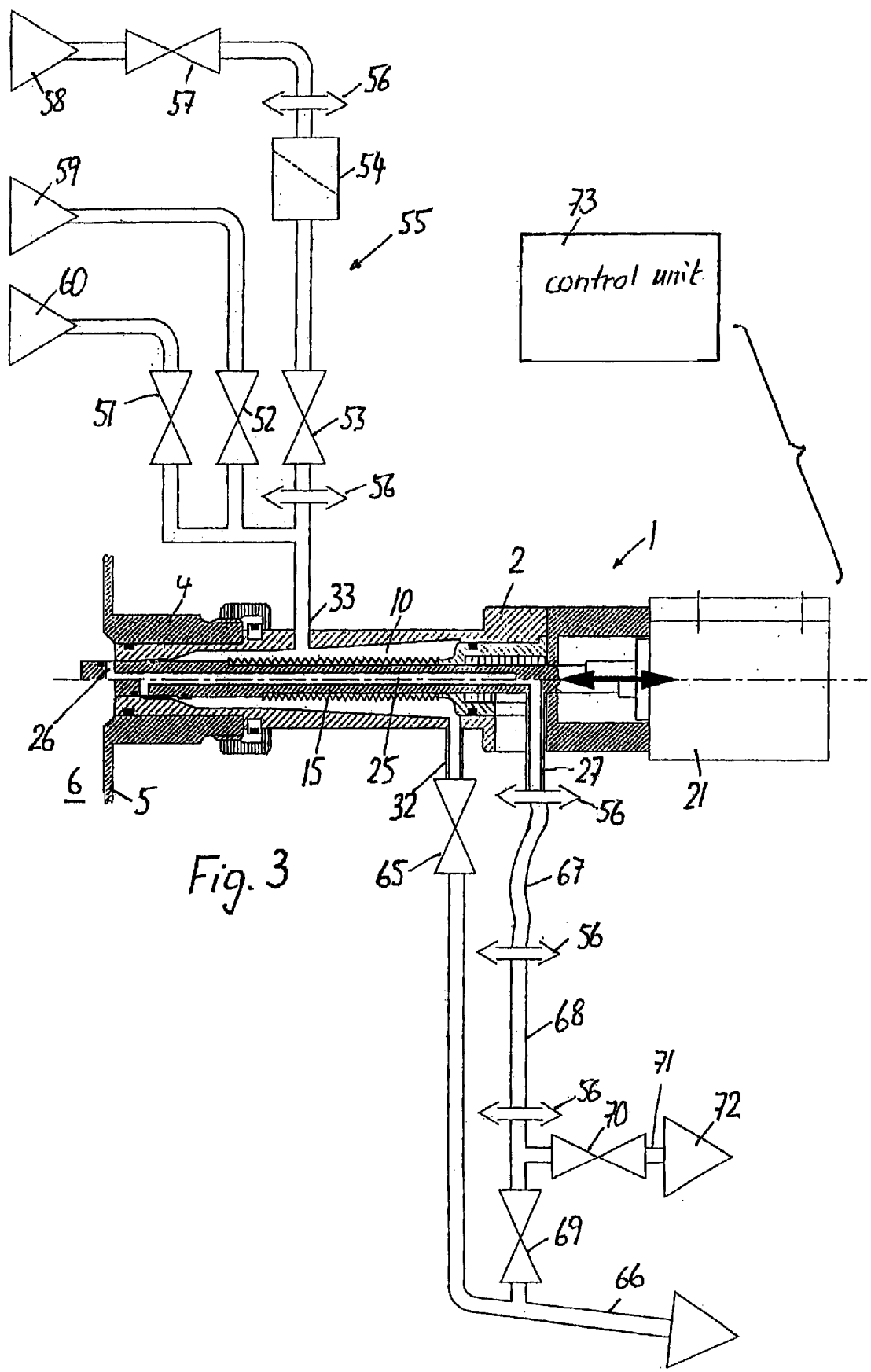
FIGS. 3 and 4 show two embodiments of the sampling device.

A sampling valve 1 presented in FIGS. 1a through 1d has a cylindrical casing 2, which is connected in a sealed-tight manner on its front end with a union nut 3 to a nozzle 4 of a hollow body 5. The hollow body 5 may be, for example, a reaction container for a liquid chemical, for cell suspensions, or a line for liquids of that type. The nozzle 4 is arranged below the fluid level in the interior space 6 of the body 5. The casing 2 has a coaxial, tapered opening 7, which is open towards the interior space 6, with a narrower cylindrical section 8 that faces towards the interior space 6, and a second cylindrical section 9 of a larger diameter. The section 9 opens into a valve chamber 10. Extending through same is a valve stem 15, which is guided in a sealed-tight manner on its unattached end inside the opening 7. For this purpose the stem 15 has two O-rings 16, 17. The stem 15 is depicted in the upper half of FIG. 1a in its extended position and in the lower half in its retracted position.

At its opposite end, the stem 15 is guided inside a further bore 18 of an insert 22, which is firmly attached to the casing 2. At this end, the stem 15 is sealed relative to the casing 2 with a metal bellows 19, one end of which is welded to the stem 15 and the other end of which is welded to the insert 22. The rear end of the stem 15 is connected to the lifting device 20 of an actuation element 21, e.g., of a pneumatic cylinder, which is fastened to the casing 2.

Extending through the stem 15 is a longitudinal bore 25, which is closed at both ends, and near its front end opens into at least one cross bore 26 between the O-rings 16, 17. Near the opposite (rear) end the bore 25 opens into a perpendicularly projecting connecting branch 27, which is welded to the stem 15 and extends through an opening 28 of the casing 2.

The valve chamber 10 is slightly conical, with its largest diameter at the end that faces the actuation element 21. At this end, the chamber 10 has on its underside a connecting branch 32. On its top the chamber 10 has a second connecting branch 33.

FIG. 1b shows the one end position of the stem 15 in which the cross bore 26 opens into the interior space 6 and the O-ring 17 seals in section 9. FIG. 1d shows the second end position, in which the cross bore 26 opens into section 9 and is, therefore, connected to the valve chamber 10. The O-ring 16 seals in section 8. FIG. 1c shows an intermediate position in which both the O-ring 16 seals in section 8 and the O-ring 17 seals in section 9, so that the cross bore 26 is sealed in both axial directions in the opening 7.

FIGS. 2a through 2d show a second embodiment. The sampling valve 1 is designed identical to the one in FIG. 1, except that the stem 15 has a coaxial, cylindrical extension 36 with a further O-ring 37. The casing 2 in this case is fastened to a nozzle 38 of an immersion pipe adapter 39, which is fastened in a sealing-tight manner to the, in this case vertical, nozzle 4. The adapter 39 has two chambers 41, 42, which are separated from one another by a separating wall 40. An immersion pipe 43 is connected to the chamber 41, which faces the opening 7. The separating wall 40 has a through bore 44 coaxial to the opening 7, inside which the O-ring 37 seals when the stem 15 is in its extended position.

The illustrations in FIGS. 2b through 2d correspond to those in FIGS. 1b through 1d.

FIG. 3 shows a fully automatic device containing the sampling valve 1 according to FIG. 1a for a periodic loss-free withdrawal of, e.g. 10 ml of fluid, in regular intervals. Three valves 51, 52, 53 are connected to the nozzle 33 via T-pieces. Valve 53 has a sterile air filter 54 connected in series. The unit 55, comprising the valve 53 and the filter 54, is connected, via removable couplings 56, to a further valve 57 and via same to a compressed-gas source 58. The unit 55 can be sterilized in an autoclave. Depending on the nature of the fluid to be sampled, the compressed gas may be air, nitrogen or an inert gas. The valve 52 is connected to a source 59 for a cleaning fluid. The source 59 may also contain a plurality of fluids, such as acids, alkaline solutions, tap water, neutralizing agents, which are transported to the valve 52 one after another. The valve 51 is connected to a source 60 for a sterilization medium, such as steam.

The nozzle 32 is connected to a discharge line 66 via a valve 65. The nozzle 27 is connected, by means of a suitable coupling 56, via a flexible line 67 and an exchangeable rigid line 68 to two further valves 69, 70. The valve 69 connects the line 68 to the discharge line 66, and the valve 70 connects it to a line 71, which connects to a device for treating or bottling the sample. The sampling valve 1 and all other valves 51–53, 57, 65, 69, 70 are connected to a control unit 73, by which the actuation of the valves is controlled based on a programmed sequence.

In the operation, the device functions as follows: The sampling valve 1, which is firmly mounted on the container 5, as well as the bores 25, 26, the nozzle 27, and the lines 67, 68 are sterilized by opening the valve 51 and pulsating the valves 65 and 69, and the downward arrangement of the nozzles 27, 32 and the conic shape of the chamber 10 ensure that the condensing water runs off. The stem 15 is in its retracted position according to FIG. 1d. The valves 52, 53 are closed. Additionally, the line 71 may be sterilized by opening the valve 70.

The valves 51, 65, 69, 70 will then be closed. When the casing 2 cools off, the remaining steam condenses and a vacuum forms in the valve chamber 10 and inside the bore 25 and the lines 67, 68. To take a sample, the stem 15 is switched into the position according to FIG. 1b. The vacuum causes the bore 25, the nozzle 27 and the lines 67, 68 to be filled with the liquid to be sampled from the container 5. The collected fluid volume may be altered by exchanging the line 68 with one having a different interior diameter or a different length. At any rate, this volume can be exactly reproduced. The valve 53 is then opened so that sterile compressed air is supplied to the chamber 10. When the stem 15 is switched to the position according to FIG. 1d and the valve 70 is opened, the compressed air pushes the drawn sample virtually completely into the device 72. This is because the valve 69 can be arranged so that any liquid located in its feeder line also drains off towards the line 71. The valve 53 will then be closed.

The lines 67, 68, 71, the nozzle 27 and the bores 25, 26 are subsequently flushed out with the cleaning fluid, which is then blown out during the following sterilization by opening the valves 52, 69, 70.

The described process can periodically repeat itself automatically. The described device and mode of operation has the following advantages: a defined, reproducible quantity can be taken from a sterile container.

Sampling can be performed in a simpler and technically less complex process than through an immersion pipe.

The clearance-volume free operation guarantees that a sample taken always reflects the current process.

Sterilization of the valve and cleaning of the same take place in situ, i.e. on location, in the installed condition and can be repeated as often as desired, without running the risk of a biological contamination when a subsequent sample is taken.

The process can be automated.

The process is suitable both for sampling from sterile containers as well as from sterile lines.

The sample is transported in its entirety (except for wetting effects on the interior walls).

The loss of medium is extremely low.

Since the cross bore 26 is closed off in both axial directions in the intermediate position according to FIG. 1c, no compressed gas can escape from the valve chamber 10 into the container 5.

Due to the small diameter, e.g. 4 mm, of the bore 25 and the lines 67, 68, 71, the contact area between the expelling compressed gas and the sample is very small. This minimizes the risk of foaming or oxidizing (in the case of air) the fluid.

Figure 4:
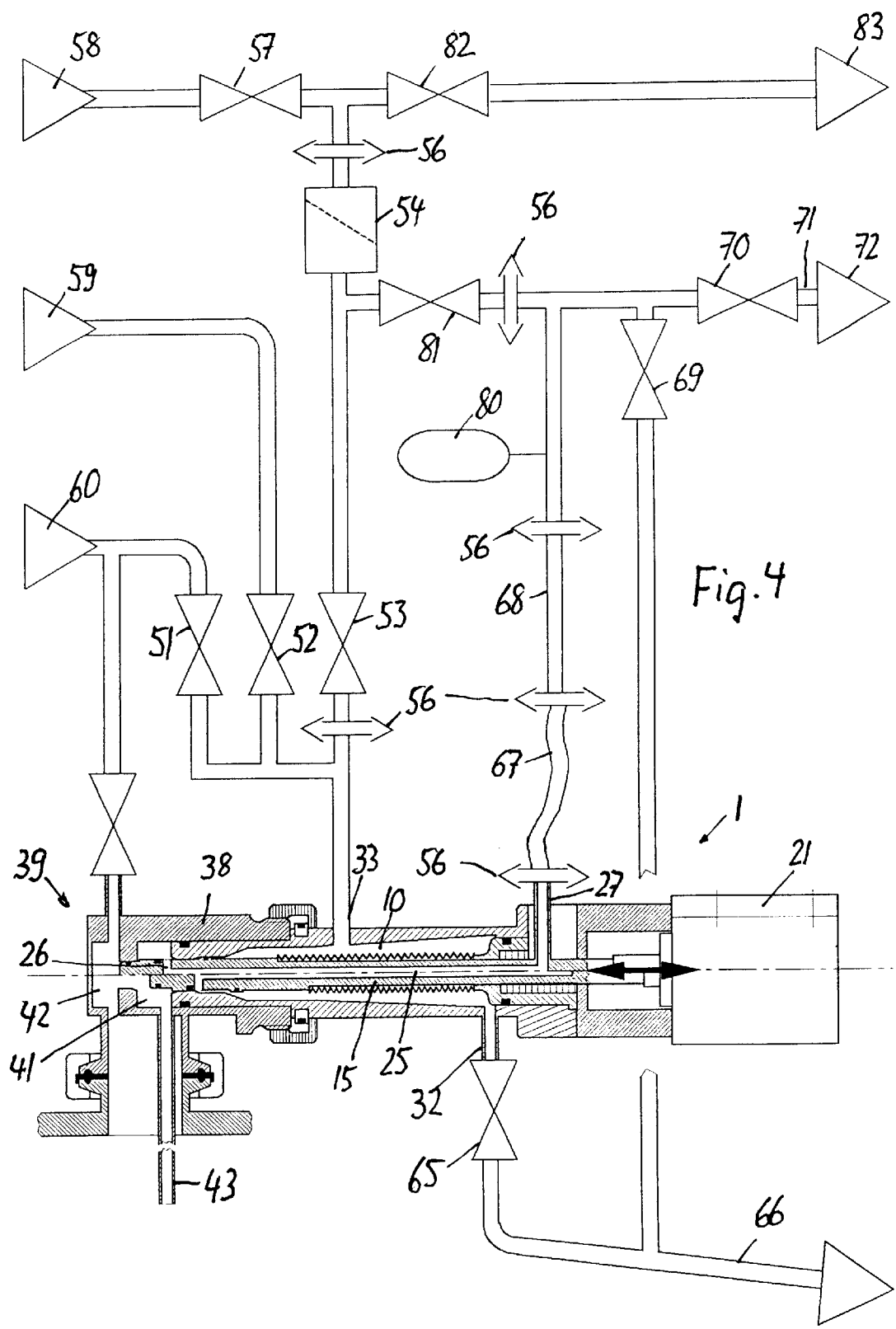

In the device depicted in FIG. 4, analogous parts are marked with identical reference numerals so that a detailed description of these parts is unnecessary. The application of the sampling valve 1 is one as shown in FIG. 2. The nozzle 27 and the lines 67, 68 point upward. The line 68 has a level sensor 80 connected in series for the fluid to be sampled, e.g., in the form of a light barrier through a transparent line. The output of this sensor 80 is connected to the sterile gas side of the filter 54 via a further valve 81, and the input of the filter 54 is connected via a further valve 82 to a suction pump 83.

In the operation, the depicted device functions as follows: The stem 15 is initially in its retracted position according to FIG. 2d. The valves 52, 69 are opened and the valve 65 is opened periodically so that the bore 25, the lines 67, 68 and the sensor 80 as well as the valve chamber 10 are flushed out. The valve 69 will now be closed and the valve 70 will be opened so that the line 71 to the autosampler 72 is flushed out as well. After cleansing with water and/or an alkaline solution, the liquid is blown out of all lines and chamber 10 by closing the valve 52 and opening the valve 53 in such a way that the valves 69, 70 are opened alternately and the valve 65 is opened periodically.

For the sterilization sequence, the valve 53 will next be closed and the valve 51 will be opened. The condensate is then drained via the pulsating valves 65, 69.

To take the sample, the valves 51, 65, 69, 70 will initially be closed and the stem 15 will be extended so that the bore 44 is closed. To expel the fluid still contained in the immersion pipe 43, which would not yield a representative sample, the valves 81 and 57 will be opened first, so that the liquid inside the immersion pipe 43 is displaced by sterile gas through the lines 69, 68 and the bore 25. After the content of the immersion pipe 43 has been expelled, the liquid is drawn from the immersion pipe 43 via the pump 83 by opening the valves 81, 82. Depending on the static pressure inside the container 5, the pump 83 may be omitted. The valves 81, 80 are closed as soon as the level of the fluid being drawn reaches the sensor 80. An exactly defined fluid volume is thus again contained in the bore 25 and the lines 67, 68. The valves 53 and 57 will then be opened so that sterile gas flows into the chamber 10. Next, the stem 15 is retracted and the sample is transported by the gas, by opening the valve 70. Afterwards the device is ready for a repetition of the above process.

The embodiment according to FIGS. 2a through 2d has the added advantage that the sample can be taken from a nozzle that is located above the fluid level in container 5. The immersion pipe is emptied prior to extracting the sample. This ensures that the sample taken reflects the current status of the process. After the sampling the immersion pipe 43 communicates with the headspace of the sterile tank so that the fluid level balances with that in the container.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A sampling valve comprising a casing (2) with a valve chamber (10) inside of which a valve stem (15) is positioned, a first end of the valve stem being connected to a lifting device (20, 21), and the second end of the valve stem being guided in a sealed-tight manner inside an opening (7) of a casing wall, wherein the valve stem (15) has a longitudinal bore (25), which, adjacent to said second end, opens into at least one cross bore (26), and adjacent to said first end opens into a connecting branch (27), wherein the valve stem (15) is positionable into a first position in which the cross bore (26) is located outside the opening (7) and into a second position in which the cross bore communicates with the valve chamber (10), wherein the cross bore (26) in an intermediate position between said first and second positions is sealed both relative to the outside as well as relative to the valve chamber (10), and wherein the valve chamber (10) has a first connection (33) for supply of a choice of one of the following media: sterilization medium, sterile gas and cleaning fluid, and a second connection (32) for draining off condensate or cleaning fluid.

2. A sampling valve as set forth in claim 1, wherein the valve stem (15), adjacent to said first end, is sealed relative to the casing (15) by an elastically deformable sealing element (19), one side of which is rigidly connected to the valve stem (15) and the other side of which is rigidly connected to a part (22) connected to the casing (2).

3. The sampling valve of claim 2 wherein said elastically deformable sealing element is a bellows or a membrane.

4. A device for a low-loss taking of samples of a fluid from the interior space of a hollow body (5) comprising a sampling valve as set forth in claim 1, wherein the casing (2) is connectable in a sealing-tight manner to the hollow body (5) in such a manner that the opening (7) faces the interior space (6) of the hollow body (5), wherein the first connection (33) has a first valve (51) connected for the supply of a sterilizing agent, a second valve (52) for the supply of a cleaning fluid, and a third valve (53) for the supply of a sterile gas, and the second connection (32) is connected to a fourth valve (65).

5. A device as set forth in claim 4, wherein the hollow body (5) is a container or a line.

6. A device as set forth in claim 4, wherein a connecting nozzle (27) is connected via a fifth valve (70) to a sample transfer line (71) and wherein said connecting nozzle (27) is connected to a discharge line (66).

7. A device as set forth in claim 6, wherein the connecting nozzle (27) is connected to the discharge line (66) via a sixth valve (69).

8. A device as set forth in claim 7, wherein the connecting nozzle (27) is additionally connectable via a seventh valve (81) to a source (54, 58) for sterile compressed gas.

9. A device as set forth in claim 8, wherein an eighth valve (57) to connect to the compressed-gas source (58) and a ninth valve (82) to connect to a vacuum source or to atmospheric pressure are connected on an incoming line before the seventh valve (81); and wherein a sensor (80) for measuring the fluid lever is provided in the line between the connecting nozzle (27) and the seventh valve (81).

10. A device as set forth in claim 8, further comprising a metering device (68, 80) for metering the sample.

11. A device as set forth in claim 6, wherein the casing (2) is connected to an immersion pipe adapter (39), wherein the adapter (39) is divided by a separating wall (40) into a first chamber (41) facing the valve chamber (10) and a second chamber (42), wherein the immersion pipe (43) is connected to the first chamber (41), wherein the separating wall (40) has a through bore (44) coaxial to the stem (15), and wherein the stem (15) has an extension (36) which closes the through bore (44) in a sealed-tight manner when in the first position.

12. A device as set forth in claim 4, further comprising a metering device (68, 80) for metering the sample.

13. A device as set forth in claim 4, wherein the third valve (53) has a sterile has filter (54) connected on the incoming line side, and wherein a unit (55) comprising the third valve (59) and the sterile gas filter (54) is removably connected via a coupling (56) to the remainder of the device, and wherein said unit (55) is autoclavable.

14. A device as set forth in claim 4, wherein the sampling valve (1) and all other valves are connected to a control device (73) for automatic sampling cleaning and sterilization.

15. A device for a low-loss taking of samples of a fluid from the interior space of a hollow body (5), comprising a sampling valve as set forth in claim 4, wherein the casing (2) is connectable in a sealing-tight manner to the hollow body (5) in such a manner that the opening (7) faces the interior space (6) of the hollow body (5), wherein the first connection (33) has a first valve (51) connected for the supply of a sterilizing agent, a second valve (52) for the supply of a cleaning fluid, and a third valve (53) for the supply of a sterile gas, and the second connection (32) is connected to a fourth valve (65).

16. A device as set forth in claim 15, wherein the hollow body (5) is a container or a line.

17. A device as set forth in claim 15, wherein a connecting nozzle (27) is connected via a fifth valve (70) to a sample transfer line (71) and wherein said connecting nozzle (27) is connected to a discharge line (66).

18. A device as set forth in claim 17, wherein the connecting nozzle (27) is connected to a discharge line (66) via a sixth valve (69).

19. A device as set forth in claim 18, wherein the connecting nozzle (27) is additionally connectable via a seventh valve (81) to a source (54, 58) for sterile compressed gas.

20. A device as set forth in claim 19, wherein the seventh valve (81) has an eighth valve (57) connected on an incoming line side to connect to the compressed-gas source (58), and a ninth valve (82) to connect to a vacuum source or to atmospheric pressure, and wherein a sensor (80) for measuring the fluid level is provided in the line between the connecting nozzle (27) ad the seventh valve (81).

21. A device as set forth in claim 20, further comprising a metering device (68, 80) for metering the sample.

22. A device as set forth in claim 21, wherein the third valve (53) has a sterile has filter (54) connected on the incoming line side, and wherein a unit (55) comprising the third valve (59) and the sterile has filter (54) is removably connected via a coupling (56) to the remainder of the device, and wherein said unit (55) is autoclavable.

23. A device as set forth in claim 22, wherein the sampling valve (1) and all other valves are connected to a control device (73) for automatic sampling, cleaning and sterilization.

24. A device a set forth in claim 17, wherein the casing (2) is connected to an immersion pipe adapter (39), wherein the adapter (39) is divided by a separating wall (40) into a first chamber (41) facing the valve chamber (10) and a second chamber (42), wherein the immersion pipe (43) is connected to the first chamber (41), wherein the separating wall (40) has a through bore (44) coaxial to the stem (15), and wherein the stem (15) has an extension (36) which closes the through bore (44) in a sealed-tight manner when in the first position.

* * * * *